United States Patent [19]

Moore

[11] Patent Number: 4,461,194
[45] Date of Patent: Jul. 24, 1984

[54] TOOL FOR SEALING AND ATTACHING A LEAD TO A BODY IMPLANTABLE DEVICE

[75] Inventor: Gary L. Moore, Brooklyn Park, Minn.

[73] Assignee: Cardio-Pace Medical, Inc., Minneapolis, Minn.

[21] Appl. No.: 372,634

[22] Filed: Apr. 28, 1982

[51] Int. Cl.³ .............................................. B25B 13/48
[52] U.S. Cl. ................................. 81/436; 128/419 P
[58] Field of Search ................ 81/429, 436, 437, 439, 81/441, 451, 452, 467, 471, 125.1, 125; 7/138; 128/419 P

[56] References Cited

U.S. PATENT DOCUMENTS

| | | | |
|---|---|---|---|
| 2,519,559 | 8/1950 | Foster et al. | 81/439 X |
| 2,917,954 | 12/1959 | Capelle | 81/439 X |
| 3,517,714 | 6/1970 | Desbarats | 81/451 |
| 3,649,367 | 3/1972 | Purdy | 136/202 |
| 3,683,932 | 8/1972 | Cole | 128/419 |
| 3,683,933 | 8/1972 | Mansfield | 128/419 |
| 3,735,766 | 5/1973 | Bowers et al. | 128/419 |
| 3,757,789 | 9/1973 | Shanker | 128/404 |
| 3,760,332 | 9/1973 | Berkovits et al. | 339/66 |
| 3,822,707 | 7/1974 | Adducci et al. | 128/419 |
| 3,824,556 | 7/1974 | Berkovits et al. | 339/268 |
| 3,842,842 | 10/1974 | Kenny et al. | 128/419 |
| 3,866,616 | 2/1975 | Purdy et al. | 128/419 |
| 3,871,382 | 3/1975 | Mann | 128/419 |
| 3,908,668 | 9/1975 | Bolduc | 128/419 |
| 3,951,154 | 4/1976 | Hartlaub | 128/419 |
| 4,010,760 | 3/1977 | Kraska et al. | 128/419 |
| 4,027,678 | 6/1977 | van Oostveen et al. | 128/419 |
| 4,037,277 | 7/1977 | Shipko | 7/138 |
| 4,072,154 | 2/1978 | Anderson et al. | 128/419 |
| 4,105,037 | 8/1978 | Richter et al. | 128/419 |
| 4,112,953 | 9/1978 | Shanker et al. | 128/419 |
| 4,141,752 | 2/1979 | Shipko | 128/419 |
| 4,180,078 | 12/1979 | Anderson | 128/419 |
| 4,221,249 | 9/1980 | Mazzeo et al. | 81/451 X |
| 4,262,673 | 4/1981 | Kinney et al. | 128/419 P |

OTHER PUBLICATIONS

"Cement in Wrench Holds Nuts", *Popular Science*, p. 192, Aug. 1946.

*Primary Examiner*—James G. Smith
*Attorney, Agent, or Firm*—Kinney & Lange

[57] ABSTRACT

A tool both attaches and seals a lead to an body implantable device such as a heart pacemaker, an insulin pump, or the like. The tool includes a handle portion and a first wrench and preferably a second wrench, with each wrench being attached to the handle portion on opposite ends thereof. The first wrench extends first through a cap and then a sealing member, the sealing member preferably made of a silicone rubber. The cap is frictionally held on the first wrench preferably by a cylindrical member circumferentially engaging the cap and fixedly attached to the handle portion. A set screw is preferably detachably attached at the end of the first wrench adjacent the sealing member. To attach the lead to the device, the set screw is threadably inserted into a bore in the device positioned at a substantially right angle to a portion of the lead, and clamps the terminal pin against an inside surface of a terminal block in the device. While the set screw is being inserted within the bore, the cap which is frictionally held by the cylindrical tube is also turned into the bore. When the set screw is turned sufficiently far to attach the electrode to the device, the first wrench is withdrawn, leaving the set screw, the sealing member and the cap within the bore. The tool is then turned around and the second wrench is used to turn the cap a remaining distance into the bore, thus deforming the sealing member such that the sealing member forms a seal around the set screw, which prevents body fluids from seeping past the sealing member and coming into contact with the set screw, the lead or the terminal block.

18 Claims, 4 Drawing Figures

TOOL FOR SEALING AND ATTACHING A LEAD TO A BODY IMPLANTABLE DEVICE

BACKGROUND OF THE INVENTION

1. Field of the Invention

The present invention relates to attaching electrode leads to body implantable devices, such as heart pacemakers and insulin pumps. In particular, the present invention relates to a tool that both connects the lead to the device and seals that connection preventing body fluids from entering therein.

2. Description of the Prior Art

Implantable electric body devices, such as a heart pacemaker an insulin pump, or the like, are well known in the art. In the case of a pacemaker, the device generally includes a pulse generator having a power source, such as a battery and associated electrical circuitry within a sealed protective casing which is substantially inert to body fluids and tissue. The electrical circuitry of the pulse generator is adapted to be connected by a lead or leads to one or more electrodes which are placed in a desired spot within a human body to which electrical pulses to regulate cardiac function are supplied. In an insulin pump, a glucose sensor is connected to the electrical circuitry of the pump to regulate the amount of insulin to be introduced into the body for control of the glucose level.

In the implantation of the stimulator and lead, it is common practice for the surgeon to place the distal end of the lead (which forms the electrode) at the desired spot within a human body and to thereafter connect the opposite end of the lead (which is typically a terminal pin or pins) to a connector assembly associated with the electrical circuitry of the device.

In a pacemaker, the connector assembly includes a terminal block imbedded in an insulating epoxy top and having two bores at substantially right angles to each other. The terminal block is connected by means of an insulated feed-through to the circuitry within the sealed casing. The terminal pin is positioned through one bore and a set screw is inserted into the other bore, thereby clamping the terminal pin against an inside surface of the block and ensuring electrical contact with the lead and the circuitry of the stimulator. To preclude electrical leakage through body fluids, the terminal block must be sealed against the penetration of such body fluids. The electrical lead, typically, has a seal made of a molded ring which is attached to the outer periphery of the lead adjacent the bore and forms a seal when the lead is inserted into the bore, preventing body fluids from seeping therein.

Sealing off the set screw is, however, a somewhat more difficult problem and various methods have been developed in trying to solve this problem. One typical method is illustrated in the Adducci et al U.S. Pat. No. 3,822,707 wherein the terminal pin of the lead is inserted into the connector block and a set screw is inserted in a threaded bore to firmly hold the electrode in contact with a surface on the interior of the connector block. Following the insertion of the set screw, a plug seal is inserted in a separate step to perfect a fluid tight seal. In the Bolduc Patent 3,908,668, a set screw is partly screwed into the connector block and the hole is filled with a grommet having a pair of protrusions. A tool is guided by the protrusions for breaking through the grommet and turning the set screw. The grommet is "self-sealing". However, difficulties arise if the tool does not engage the set screw properly after piercing the grommet in an opertion as delicate as a pacemaker implant. The Kraska et al Patent 4,010,760, shows a similar method of sealing the set screw from body fluids.

The Anderson et al U.S. Pat. No. 4,072,154 uses a set screw and a plug arrangement wherein the set screw is inserted first and the plug later inserted into the opening to effect the seal. The Anderson U.S. Pat. No. 4,180,078 also shows a similar arrangement.

The Richter et al U.S. Pat. No. 4,105,037 illustrates an arrangement where a set screw is first inserted and a "silicone medical adhesive" is subsequently used to fill the opening around the head of the screw.

A further arrangement is illustrated in the Schipko et al U.S. Pat. No. 4,141,752 which discloses a screw for holding the terminal pins of the electrical leads that includes a hard cap surrounding a screw head which is formed from a medical grade epoxy resin. An O-ring around the periphery of the screw head forms a seal to prevent body fluids from seeping to the electrode. One disadvantage that the arrangement of the Schipko et al Patent has is that threshold measurements cannot be made easily once the lead and the stimulator circuitry are connected by the set screw due to the hard epoxy head of the screw.

While all of the above references show arrangements of sealing the set screw, problems in inserting the set screw and sealing occur. The set screw used to connect the electrode to the stimulator is quite small and if a plug is used to seal the set screw, the plug is also quite small. From time to time, one or the other is lost on or near the operating table. In addition, due to their small size, both are quite difficult to handle directly by hand, which is quite undesirable during surgery.

SUMMARY OF THE INVENTION

The present invention includes a tool for attaching and sealing an electrode to a body implantable device, such as a heart pacemaker, an insulin pump, or the like. The device has a terminal block wherein a terminal pin of a lead is inserted through a bore for electrical connection with circuitry of the implantable device. A second bore communicating with the first bore is preferably threaded to receive a set screw.

The tool includes a handle portion to which is connected a first wrench and preferably a second wrench on opposite ends of the handle. A rigid cap and a sealing member made of a soft sealing implantable medical grade elastomeric material are positioned on the first wrench with the rigid cap nearest the handle portion. A set screw is positioned on the end of the wrench adjacent the sealing member and is preferably held on the end of the first wrench with a medical grade adhesive. The rigid cap is frictionally held in a predetermined spaced relationship from the set screw, preferably, by a cylindrical tube frictionally engaging the periphery of the cap and fixedly attached to the handle portion. The rigid cap and the second wrench are designed such that the second wrench is used to drive the cap and compress the sealing member, thus providing a leak-proof seal.

In practice, a physician picks up the tool with the set screw, sealing member and cap arrangement as described above and positions the set screw within the bore of the implantable device's terminal block. As the set screw is driven into the bore, the screw forces the terminal pin into a firm physical engagement and electrical contact with the terminal block. Simultaneously, as the set screw is driven within the bore, the rigid cap being frictionally held by the cylindrical tube is also partially threadably engaged within the bore. When the first wrench is removed from the set screw, the rigid cap detaches from the cylindrical tube and the first wrench, leaving the set screw, the sealing member and the rigid cap within the bore of the connector block. Subsequently, the tool is turned end-for-end and the second wrench is used to drive the rigid cap the remaining distance into the bore, thereby compressing the sealing member such that a seal is formed to prevent body fluids from reaching the set screw, the terminal block, or the electrode lead.

DETAILED DESCRIPTION OF THE PREFERRED EMBODIMENTS

Figure 1:
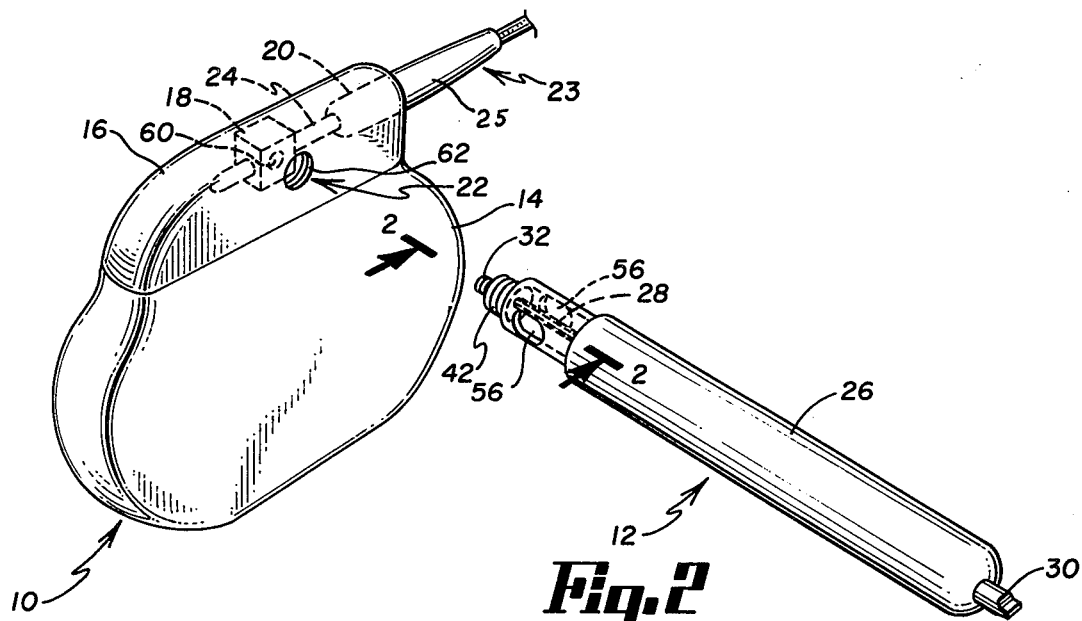
FIG. 1 is a perspective view of the tool of the present invention in working alignment with a heart pacemaker.
Figure 2:
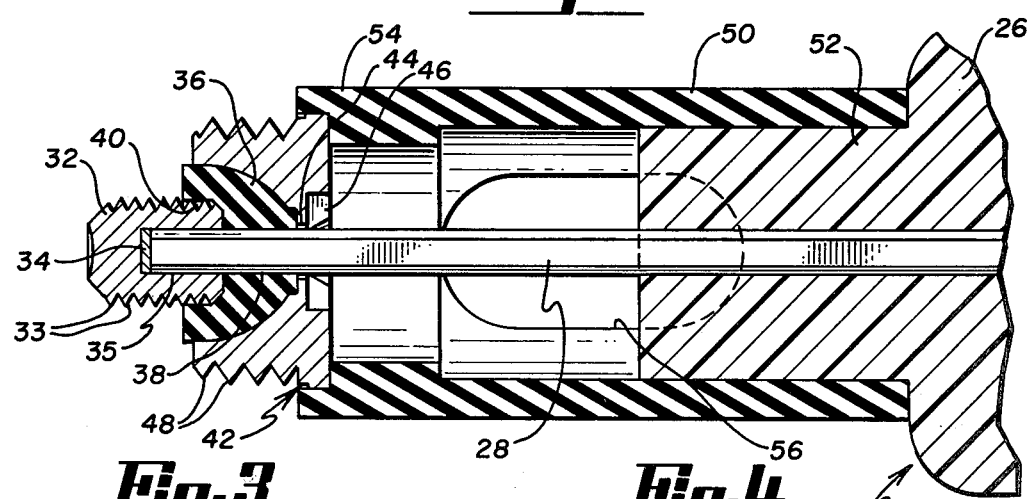
FIG. 2 is an enlarged fragmentary cross sectional view of the tool taken along the line 2—2 in FIG. 1.

An example of a body implantable device, such as a heart pacemaker 10, is generally indicated in FIG. 1 with a tool 12 of the present invention. Although the detailed description of the preferred embodiment is directed to a heart pacemaker, it should be understood that the present invention is used with other body implantable devices, such as an insulin pump for connecting a glucose sensor to the insulin pump. The heart pacemaker 10 includes a housing 14 and top 16 made of a nonconductive material, such as epoxy. The epoxy top 16 typically includes a terminal block 18 made of a suitable conductive material with two bores 20, 22 at substantially right angles to each other. The bores 20 and 22 extend from the terminal block 18 through the epoxy top 16. The terminal block 18 is electrically connected to a pulse generator within the housing 14 by means of an insulated feed-through (not shown) which extends through the top of housing 14. A lead 23 is inserted into the bore 20 for making electrical connection between terminal pin 24 and the terminal block 18. The lead 23 has a sealing section 25 preferably made of a medical grade elastomeric material, such as silicone rubber or polyurethane which is compressed by an interior surface of the bore 20 upon insertion of the lead 23 to form a seal. The terminal block 18 is used to electrically connect the terminal pin 24 of the lead 23 to the pulse generator circuitry within housing 14. The distal end of the lead 23 is an electrode (not shown) which is connected to terminal pin 24 by an electrical conductor (not shown) which extends through lead 23. This electrode is placed in a desired spot within a human body and applies electrical pulses from the pulse generator to body tissue to regulate bodily functions, such as cardiac functions. Alternatively, the electrode can be used as a sensor.

To ensure electrical contact between the terminal pin 24 and the terminal block 18, a set screw 32 is threadably inserted into the bore 22, thereby clamping the terminal pin 24 against an inside surface of the terminal block 18 to ensure physical connection and electrical contact therewith. After the terminal pin 24 has been clamped by the set screw 32, the terminal block 18 and the set screw 32 must be sealed against the penetration of body fluids. Inserting the set screw 32 and thereafter sealing the electrical connection has in the past been a difficult task since the set screw 32 is quite small, typically being a 2–56 size set screw, and consequently difficult to handle which is quite undesirable during surgery.

The tool 12 of the present invention is provided for eliminating the difficulty of handling the small set screw 32 and the subsequent sealing thereof. The tool 12 is an integral tool having a handle portion 26, a hex wrench 28 fixedly attached to one end and a slotted wrench 30, similar to a screwdriver, fixedly attached to an opposite end of the handle portion 26. Preferably, the slotted wrench 30 and the handle portion 26 are made of one integral piece of plastic. In one successful embodiment of the present invention, the handle portion was approximately three inches long and approximately ⅜ inch in diameter.

The set screw 32, which is preferably made of metal, is positioned and removably attached on the free end of the hex wrench 28 by a small drop of medical grade silicone adhesive 34. The set screw 32 has a hex-shaped recess 35 to receive the free end of the hex wrench 28. A sealing plug 36, preferably made of a suitable medical grade elastomeric material, such as silicone rubber, that is easily deformed, is positioned behind the set screw 32 with the hex wrench 28 extending through an aperture 38. The plug 36 includes a recess 40 which frictionally engages a portion of the threads 33 of the set screw 32 helping to hold the set screw on the end of the hex wrench 28.

A cap 42 having an aperture 44 for receiving the hex wrench 28 and a slot 46 for receiving the slotted wrench 30 is positioned on the hex wrench 28 on a side of the plug 36 opposite from the set screw 32. It should be understood that other wrench configurations for wrench 30 are also contemplated such as a hex wrench configuration. The cap 42 is preferably made of a medical grade plastic such as Delrin manufactured by E. I. Dupont de Nemours Co., Inc. The cap 42 also preferably has threads 48 for engaging the bore 22 of the epoxy top 16.

The wrench 30 is a self-limiting type torque wrench, preventing over-torquing of the cap 42 within the bore 22. The cap 42 is tightenable to a predetermined value which prevents the cap 42 from being tightened to a value that either cracks the cap or strips the threads in the bore. The wrench 30 simply flexes to prevent over-tightening.

A sleeve 50, preferably made of a medical grade silicone rubber, is fixedly attached to an end of the handle portion 26, by elastic engagement of a neck portion 52 extending from the handle portion 26. The sleeve 50 is flexible and has electrical insulating characteristics. On an end 54 opposite from the handle portion 26, the sleeve 50 frictionally engages the outer periphery of a top of the cap 42 and holds the cap a predetermined distance from the set screw 32. Preferably the sleeve 50 is transparent or semi-transparent to allow viewing therethrough and has at least one opening 56 (and preferably two openings 56) providing access to the hex wrench 28.

The flexibility of the sleeve 50 is important in allowing the cap 42 to be turned into the bore at a different rate than the set screw which is also being turned into the terminal block. The different threading rates of the set screw and bore permit different thread pitches in each. Preferably, a coarser pitch thread is used in the epoxy top 16 which is easier to mold, easier to start threaded engagement with the cap 42 and more reliable. The sleeve 50 provides twisting flexibility and linear flexibility along the axis of the wrench assembly.

To connect the terminal pin 24 to the terminal block 18 of the pacemaker 10 using the tool 12 of the present invention, the terminal pin 24 is placed within the bore 20. The tool 12 is then held directly by hand and the set screw 32 inserted within the bore 22. The set screw 32, the plug 36 and the cap 42 are all substantially coaxially positioned on the wrench 28.

Figure 3:
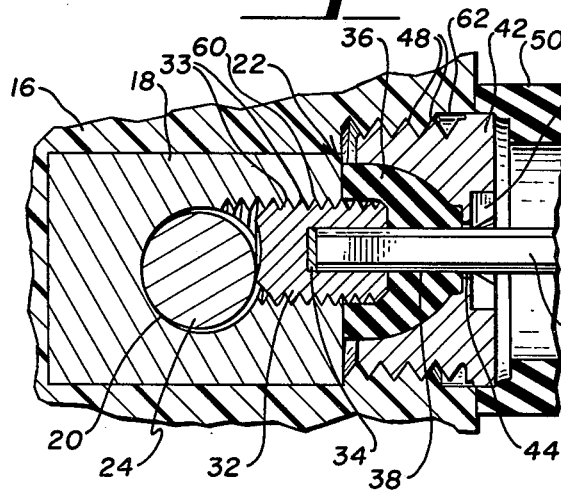
FIG. 3 is a fragmentary cross sectional view illustrating the clamping of an electrode lead using the tool of the present invention.
Figure 4:
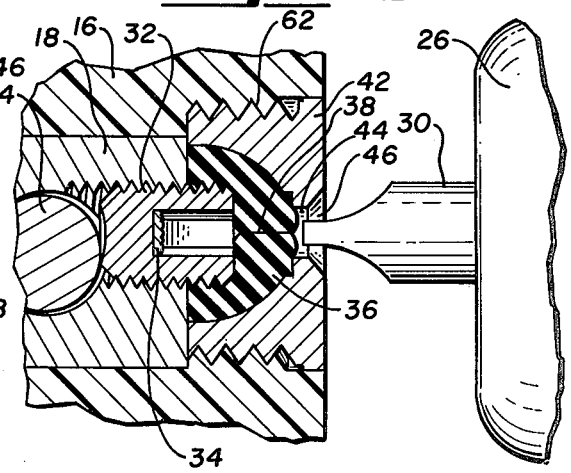
FIG. 4 is a fragmentary cross sectional view illustrating the sealing of the set screw and electrode using the tool of the present invention.

The bore 22 preferably includes two threaded sections as illustrated in FIGS. 3 and 4. A first threaded section 60 is positioned within the terminal block 18 and has a diameter to accommodate the set screw 32. A second threaded section 62 is positioned within the epoxy top 16 and has a diameter to accommodate the cap 42. As the set screw 32 is threaded into the section 60, the cap 42 also engages the threads of the section 62. The cap 42 engages the section 62 only after the set screw has been substantially threaded into the bore 20 due to the predetermined distance that the cap 42 is spaced from the set screw 32. The sleeve 50 frictionally holds the cap 42 while the cap 42 is partially threaded within the section 62. When the set screw 32 is completely threaded within the section 60, the set screw 32 holds the terminal pin 24 against the inside surface of the bore 20. The hex wrench 28 is then removed, disengaging from the set screw 32, and leaving the cap 42 and the silicone sealing plug 36 within the epoxy top of the pacemaker 10.

To seal the electrical connection from body fluids, the tool 12 is reversed end-for-end and the slot-type wrench 30 is placed within the slot 46 of the cap 42. The cap 42 is tightened, thereby compressing and deforming the silicone rubber seal 36, as illustrated in FIG. 4. The silicone rubber seal 36 is compressed such that the seal completely closes off the aperture 38 through which the hex head wrench 28 previously extended.

The hex wrench 28 of the present invention is also a self-limiting type torque wrench. In other words, the set screw 32 is tightenable to a predetermined value and if the wrench is turned past the predetermined value, the hex wrench 28 will twist. The hex wrench 28 is preferably made of titanium and more preferably an annealed titatium alloy which permits the hex wrench 28 to be twisted without fracturing.

The self-limiting torque feature of the hex wrench 28 is quite helpful since physicians often have a tendency to overtighten the set screw to ensure electrical contact between the terminal pin 24 and the terminal block 18. Overtightening the set screw 32 can result in one of three situations. The threads on the set screw 32 can be ruined, the threads 60 on the connector block can be ruined, or the hex slot 35 within the set screw 32 can be rounded. If the set screw 32 needs to be removed during the same operation or in the future to replace the pacemaker 10, it is difficult if not impossible to remove the set screw 32 from the aperture 60 if any one of the three mentioned situations has occurred. However, using the hex wrench 28 of the present invention, the set screw 32 or the bore cannot be damaged and the set screw 32 is easily removed.

As mentioned previously, the hex wrench 28 when twisted does not fracture. Since the wrench 28 will not fracture when twisted, no part of the wrench will be left in the set screw as the case in prior art devices which are designed to break beyond a predetermined torque value.

Another advantage of the present invention assists the surgeon in taking threshold measurements in evaluating whether the electrode is in the proper place in the heart. Threshold measurements can be made in a simple manner using the tool 12 of the present invention. Prior to tightening down the cap 42, the surgeon places a probe or a clip in contact with the hex wrench 28 through one of the openings 56 in the sleeve 50 to connect a suitable electronic analyzer to evaluate the proper positioning of the electrode within the heart. In addition, the electrical measurements by means of the hex wrench 28 in contact with the set screw 32 can be used to determine the type of amplitude or pulse rate that is desired to stimulate the heart.

CONCLUSION

The present invention includes a tool that permits a surgeon in a simple and efficient manner to connect an implantable tissue implantable device to a lead and seal the electrical connection from bodily fluids. In addition, the tool eliminates the possibility of damage to the set screw or the terminal block during installation and provides electrical access to the tissue implantable device and the electrode during implantation of the tissue implantable device.

Although the present invention has been described with reference to preferred embodiments, workers skilled in the art will recognize that changes may be made in form and detail without departing from the spirit and scope of the invention. For example, although a unipolar pacemaker with a single lead has been specifically described, the present invention is equally applicable to devices such as a bipolar pacemaker having multiple leads. In that case, the physician is preferably provided with one tool 12 of the present invention for each lead to be connected.

What is claimed is:

1. An apparatus for attaching and sealing a lead to a body implantable device, the device having a bore exposing a terminal portion of the lead and a terminal block for connection of the lead and the terminal block, the apparatus comprising:
    a handle portion;
    first wrench means fixedly attached to the handle portion and having a shaft and a free end for transmitting rotational force from the handle;
    a set screw detachably mounted on the free end for rotation by the first wrench means and having external threads for engaging the bore, as the set screw is rotated by the first wrench means and having an end for engaging the terminal portion of the lead;
    deformable sealing means positioned adjacent the set screw on the first wrench means for sealing the bore to prevent exposure of the set screw to body fluids, the deformable sealing means having an axial passage through which the shaft extends and having a set screw engaging recess for frictionally holding the set screw;

cap means positioned on the shaft of the first wrench means adjacent the deformable sealing means on a side opposite from the set screw, the cap means having an axial passage through which the shaft passes and having external threads for engaging the bore, the cap means applying pressure to the deformeable sealing means when fully threaded into the bore to cause the deformable sealing means to seal the bore; and means for transmitting rotational force from the handle portion to the cap means to cause partial threading of the cap means into the bore as the set screw is threaded into the bore by the first wrench means.

2. The apparatus of claim 1 wherein the handle portion has first and second ends on opposite sides of the handle portion and wherein the first wrench means is fixedly attached to the first end and wherein the apparatus includes second wrench means fixedly attached to the second end of the handle for transmitting rotational force from the handle to the cap means to thread fully the cap means into the bore.

3. The apparatus of claim 1 wherein the first wrench means is a hex wrench and the set screw has a hex-shaped recess for receiving the free end.

4. The apparatus of claim 1 wherein the first wrench means twists when a predetermined torque value has been reached, the predetermined torque value being less than a torque value required to cause damage to the set screw and the bore.

5. The apparatus of claim 4 wherein the first wrench means is made of titanium.

6. The apparatus of claim 2 wherein the cap means contains a slot and wherein the second wrench means includes a blade for engaging the slot, the blade yielding at a predetermined torque value to prevent damage.

7. The apparatus of claim 1 wherein the set screw is detachably mounted on the free end of the first wrench means by an adhesive.

8. The apparatus of claim 7 wherein the adhesive is a silicone adhesive.

9. The apparatus of claim 1 wherein the deformable sealing means is made of an elastomeric material.

10. The apparatus of claim 9 wherein the elastomeric material is a silicone adhesive.

11. The apparatus of claim 2 wherein the means for transmitting rotational force from the handle portion to the cap means is a sleeve having the first end and a second end, the first end being fixedly attached to the first end of the handle portion and the second end frictionally engaging the cap means.

12. The apparatus of claim 11 wherein the sleeve is made of flexible material.

13. The apparatus of claim 11 wherein the sleeve is made of an electrically insulating material.

14. The apparatus of claim 11 wherein the set screw and the first wrench means are made of an electrically conductive material and wherein the sleeve further includes at least one opening providing electrical access to the first wrench means.

15. The apparatus of claim 2 wherein the handle portion and the second wrench means are an integral piece of plastic.

16. An apparatus for attaching and sealing a lead to a body implantable device, the device having a threaded bore exposing a terminal portion of the lead and a terminal block for connection of the lead and the terminal block, the apparatus comprising:

a handle;

a first wrench fixedly attached to the handle and having a shaft with a free end;

a set screw mounted on the free end of the first wrench and having external threads for engaging the threaded bore and having an end for engaging the terminal portion of the lead;

deformable seal means positioned on the shaft adjacent the set screw for sealing the bore to prevent exposure of the set screw to body fluids;

a cap having external threads for engaging the bore and positioned on the shaft on a side of the deformable seal means opposite from the set screw and having an axial passage through which the shaft passes, the cap applying pressure to the deformable seal means when fully threaded into the bore to cause the deformable seal means to seal the bore; and a flexible sleeve having a first end engaging the cap and a second end engaging the handle for transmitting rotational force from the handle to the cap to cause partial threading of the cap into the bore as the set screw is threaded into the bore by the first wrench; and means for drivably engaging the cap to thread the cap into the bore after the first wrench has been removed to deform the deformable seal means to seal the bore.

17. The apparatus of claim 16 wherein the bore has a first portion with a first diameter and a second portion with a second diameter with the second diameter being larger than the first diameter, the first diameter being of a size to threadably accommodate the set screw and the second diameter being of a size to threadably accommodate the cap means.

18. An apparatus for attaching and sealing a lead to a body implantable device, the device having a threaded bore exposing a terminal portion of the lead and a terminal block for connection of the lead and the terminal block, the apparatus comprising:

a handle;

a first wrench attached to the handle, the wrench having a shaft extending axially from the handle and having a free end;

a set screw positioned on the free end of the first wrench, the set screw having external threads for engaging the bore, an end for engaging the terminal portion of the lead, and a recess for engaging the free end of the first wrench to receive rotational force transmitted from the handle through the first wrench;

a flexible deformable sealing plug positioned coaxially on the wrench adjacent the set screw with the shaft extending through the plug, the plug having a set screw engaging recess;

a cap positioned coaxially on the first wrench with the shaft extending through the cap, the cap having external threads for engaging the bore;

a flexible sleeve having a first end engaging the cap and a second end engaging the handle for holding the cap substantially coaxially with respect to the first wrench and transmitting rotational force from the handle to the cap to partially thread the cap into the bore as the set screw is threaded into the bore; and a second wrench for rotating the cap after the first wrench is withdrawn from engagement with the set screw and plug to thread the cap further into the bore to apply force to the plug which causes the plug to seal the bore.

* * * * *